United States Patent
Horeman et al.

(10) Patent No.: US 10,842,475 B2
(45) Date of Patent: Nov. 24, 2020

(54) SETON FOR TREATING FISTULAE, AND A METHOD OF FORMING A CLOSED LOOP OF A SETON

(71) Applicant: MEDISHIELD B.V., Delft (NL)

(72) Inventors: Tim Horeman, Leiden (NL); Willem Nerkens, The Hague (NL); Freek Van Delft, Oestgeest (NL); Wilhelmus Adrianus Bemelman, Vinkeveen (NL)

(73) Assignee: Super Seton BV, Amsterdam (NL)

( * ) Notice: Subject to any disclaimer, the term of this patent is extended or adjusted under 35 U.S.C. 154(b) by 987 days.

(21) Appl. No.: 14/425,023

(22) PCT Filed: Sep. 2, 2013

(86) PCT No.: PCT/EP2013/002630
§ 371 (c)(1),
(2) Date: Feb. 28, 2015

(87) PCT Pub. No.: WO2014/032813
PCT Pub. Date: Mar. 6, 2014

(65) Prior Publication Data
US 2015/0250460 A1 Sep. 10, 2015

(30) Foreign Application Priority Data
Sep. 3, 2012 (NL) ...................................... 2009404

(51) Int. Cl.
*A61B 17/00* (2006.01)
*A61B 17/04* (2006.01)
(Continued)

(52) U.S. Cl.
CPC ...... *A61B 17/0057* (2013.01); *A61B 17/0487* (2013.01); *A61B 2017/00641* (2013.01); *A61B 2017/06019* (2013.01); *A61M 27/002* (2013.01)

(58) Field of Classification Search
CPC .... A61B 17/06004; A61B 2017/00641; A61B 2017/06038; A61B 2017/06019;
(Continued)

(56) References Cited

U.S. PATENT DOCUMENTS

| 5,089,011 A | * | 2/1992 | Korthoff | A61B 17/06004 606/224 |
| 5,622,293 A | * | 4/1997 | LeFevre | A44C 5/003 220/212 |

(Continued)

FOREIGN PATENT DOCUMENTS

| WO | 2002/022025 A1 | 3/2002 |
| WO | 2005/020823 A1 | 3/2005 |

(Continued)

OTHER PUBLICATIONS

International Search Report received for International Patent Application No. PCT/EP2013/002630, dated Jan. 14, 2014, 4 pages.
(Continued)

*Primary Examiner* — Martin T Ton

(57) ABSTRACT

A size-adjustable seton (1) for treating fistulae (32) is provided with first and second wire ends (4, 6), which are provided with connecting means (8, 10) for, in a connected state, forming a smooth connection (12); in such a way, the seton (1) is a smooth, closed loop (3). The invention also relates to a method of forming the closed loop using the aforesaid seton (1), and a melt clamp (40) for use when placing the seton (1) in a person (30).

14 Claims, 4 Drawing Sheets

(51) Int. Cl.
*A61B 17/06* (2006.01)
*A61M 27/00* (2006.01)

(58) Field of Classification Search
CPC . A61B 17/0057; A61B 17/0487; A16L 33/00; A16L 33/30; A16L 33/003; A16L 33/24; A16L 33/34; Y10T 29/49908
See application file for complete search history.

(56) References Cited

U.S. PATENT DOCUMENTS

| | | | | |
|---|---|---|---|---|
| 5,891,397 | A * | 4/1999 | Greenfield | B01L 3/502715 359/398 |
| 6,090,131 | A * | 7/2000 | Daley | A61B 17/0487 606/219 |
| 6,409,743 | B1 | 6/2002 | Fenton, Jr. | |
| 2002/0173821 | A1 * | 11/2002 | Fenton | A61B 17/0487 606/228 |
| 2008/0255611 | A1 * | 10/2008 | Hunter | A61B 17/06166 606/228 |
| 2009/0227954 | A1 * | 9/2009 | Loiterman | A61M 39/12 604/175 |
| 2009/0248071 | A1 * | 10/2009 | Saint | A61B 17/0401 606/232 |
| 2011/0015653 | A1 * | 1/2011 | Bogart | A61B 17/0487 606/139 |

FOREIGN PATENT DOCUMENTS

| | | |
|---|---|---|
| WO | 2011/068533 A1 | 6/2011 |
| WO | 2011/151659 A2 | 12/2011 |

OTHER PUBLICATIONS

International Preliminary Report on Patentability and Written Opinion received for International Patent Application No. PCT/EP2013/002630, dated Mar. 12, 2015, 7 pages.

* cited by examiner

SETON FOR TREATING FISTULAE, AND A METHOD OF FORMING A CLOSED LOOP OF A SETON

TECHNICAL FIELD

The invention relates to setons for treating fistulae, and in particular to setons for treating peri-anal fistulae. Moreover, the invention relates to methods of forming closed loops from setons, and melt clamps for use in conjunction with such methods.

STATE OF THE ART

A draining wire, also known as a seton, is a wire that is placed in a fistula channel or tract, whose ends are then mutually connected after one of the ends is cut to length, so that the draining wire assumes a form of a closed loop. The presence of the draining wire in the fistula channel ensures that the fistula channel remains open, so that a risk inflammation is reduced, and healing is promoted. Some suitable materials for manufacturing setons include: suture wire, rubber, and medicinal wire.

Setons can, for example, be used in treating peri-anal fistulae. A peri-anal fistula is an abnormal inflammatory canal formed between the anal canal and peri-anal skin. Causes for peri-anal fistulas may include Crohn's disease, other infections of anal glands, trauma, or abnormal growths.

An international PCT patent application WO2005/020823A1 describes placement of a draining wire in a peri-anal fistula channel. A probe, to which the draining wire is connected, is inserted into the peri-anal skin surface, and is then passed through a duct of the peri-anal fistula channel, and then discharged again to an outside through an associated anus. After the draining wire has been placed by means of the probe, two ends of the draining wire are mutually connected by binding them with a knot. The ends may also be secured through other well-known ways of making connections. Thereby, a so-called "loose seton" or "permanent seton" is formed, which is secured in the anal area for a long period of time in order to prevent blockage of the fistula channel. By such an approach, the fistula channel is continuously drained, and abscess formation is at least partially counteracted.

It has been shown in relation to permanent placement of the seton, according to WO2005/020823A1, that the presence of the knot is painful and leads to an uncomfortable situation for an associated patient. Moreover, the knot may also accumulate debris and may lead to further infections. Furthermore, current procedures of installation of setons lead to excessive tightening or loosening of the setons. Hence, there is a need for a simpler, smoother seton which is easier to apply, which does not cause any discomfort due to its presence or movement, and which is easily cleaned.

BRIEF DESCRIPTION OF THE INVENTION

An object of the present invention is therefore to provide a seton for treating a fistula, wherein the seton has an improved comfort for an associated patient.

According to a first aspect of the invention, this object is achieved by providing a seton that can be cut to a desired length for treating a fistula, wherein the seton includes a wire having a first wire end and a second wire end. The seton is provided with means for connecting in a longitudinal direction of the wire, wherein the wire ends are mutually secured together to form a smooth connection thereat, in such a way that the seton forms a smooth, closed loop.

Connecting the ends of the seton by means of a knot, or by means of a suture according to known methods, makes an operation of installing the seton more complex. A knotted seton is relatively difficult to keep clean, and the knot has a tendency to rotate towards an entrance to the fistula channel. The seton in accordance with this aspect of the invention is provided with connecting means, wherein the ends of the seton to be placed are mutually connected to form a smooth joint, such that the whole of a seton is in a form of a smooth closed loop. This simplifies the placing of the seton in a patient. The term "wire" should be given a broad interpretation, and here, refers to relatively elongate, namely of an order of centimeters long, thin, namely in an order of millimeters or less, flexible structures that are reported in the art, and which are deemed suitable for use as a seton. The wire may, for example, have a solid, twisted or braided structure, or, at least partially, be a hollow tube shape. By "longitudinal direction of the wire" as used herein, a local axis of the wire, which corresponds to the local tangent, may vary along the wire; in other words, the wire is elongate and may be straight, or may be curved. Moreover, "connecting means" can be understood both as a single compound structure as well as a plurality of co-acting connecting structures. According to described embodiments below, such connecting means are already present at or near the wire ends, or are added during placement of the seton by means of a special operation or to be provided near the wire ends. The term "smooth closed loop" signifies that, at the connection of the wire ends of the seton, the seton is devoid of any knot or abrupt (i.e. not smooth) thickening, which may cause channel obstruction by fixation in the fistula channel. By such an absence of knots or abrupt thickening, any portion of the placed seton may move and rotate freely through the fistula channel without discomfort to the patient. In addition, each section of the smooth closed loop is easily accessible to clean on account of rotational freedom of the seton when installed. It will be appreciated that the seton according to this aspect can also be used for applications other than treating fistulae ("fistulas") and in other locations in the human or animal body.

According to an embodiment of the seton, the connecting means comprises a thermoplastic material. The thermoplastic material in the connecting means makes it possible by a melting process to secure the wire ends of the seton together to form a smooth joint by supplying thermal energy. Suitable thermoplastic materials for the present application are, for example, polyurethane or polycarbonate. The thermal energy can easily, and quickly, be supplied in a controlled manner to the connecting means, for example, by means of a heating element or through ultrasound or radiation. The wire of the seton may also, wholly or partly, be made of the aforementioned thermoplastic material. Fusion of the thermoplastic connecting means will include a heated thermoplastic portion of the wire which melts, so that extra strength will be imparted to the resulting smooth joint.

In another embodiment of the seton, the connecting means optionally comprises a light-curable material, such as a UV-curable resin, which hardens when irradiated with, for example, ultraviolet (UV) light. Light-curable materials may come in a form of resins which are easier to apply and which do not require sophisticated apparatus, such as RF (Radio Frequency) or thermal melt clamps. The UV light is also comparatively relatively less risky to use, as a need to bring heating elements near a body of a patient is avoided. The UV-curable materials are optionally applied quickly and effectively to join mutually the two ends of the wires of the seton. This may also be done using a clamp to shape the UV-curable resin. The UV-curable resin may also be preshaped to form any of the connecting means which can then be hardened to form a tight fit for the seton.

In further alternate embodiments, the connecting means is optionally cold welded to form a smooth seton. Chemical agents are optionally present in the connecting means or the wire which melts or welds in the presence of applied pressure. Chemicals or solvents are optionally also used irreversibly to join the connecting means to the wire to form a smooth seton. Welding offers a convenience of using a simple clamp over a thermal clamp. Such an approach potentially considerably reduces a cost of manufacture and reduces risks involved in an operating procedure when installing the seton. The connecting means, such as sleeves or connector pins, are optionally manufactured from materials such a polymers, with low melting points under high pressure. These materials when subjected to high pressure during clamping are operable to melt to form a bond with the wire ends, thereby forming a smooth closed loop.

As for the fusion, the invention provides, according to another aspect of the invention, a hand-operable, and optionally partially sterlizable, melt clamp. The melt clamp allows the placement of a seton to be performed simply and quickly by employing a sterile confirmatory method employing the melt clamp. The melting of the wire and attachment method is described later according to these other aspects.

According to embodiments of the seton, the wire ends can be formed in various suitable ways. They may be formed, for example, as complementary engagement surfaces which are shaped in such a way that they form a closed compound structure. Thus, optionally, the complementary connecting surfaces are implemented in a transversal interlocking manner. A few alternative embodiments are described below.

According to an embodiment of the seton, the connecting means comprising a first recess which is provided at a first wire end with a first inner surface in a longitudinal direction of the wire, and a first insertion portion at a second wire end having a first outside surface in the longitudinal direction of the wire that is at least partially conformed to the first recess. Moreover, according to further embodiments, at least one of the two ends may be cut to alter the length of the wire which, in turn, may alter the circumference of the seton loop.

At least a portion of an outer surface of the first insertion portion of the seton has a shape corresponding to the inner surface of the first sleeve recess at the first end of the seton. This allows the insertion in a form-fitting manner, so as to connect to a terminal in the recess form. When such a plug-in part, and optionally the first wire end, comprises a thermoplastic material, then a smooth connection can be made permanently and quickly. According to further embodiments, the first plug-in part is fixed to the second wire end, or optionally the first insertion portion is formed as a separate component connector fitting in both the first recess to the first wire end, as well as in a second recess at the second wire end if it can be inserted. According to another further embodiment, the first wire end optionally comprises a thickened thermoplastic connecting structure that has a cylindrical first access along the elongate longitudinal direction of the wire. The second wire is formed as a cylindrical solid structure, with a second cylindrical end that represents the insertion portion into the first end of the wire. By melting of the thickened compound structure around the second wire end, the smooth structure is thereby formed. The length of the cylindrical wire is optionally shortened as required prior to the second wire end, for example, by executing a cutting operation.

According to a further embodiment, the wire is manufactured from flexible tube with an inner surface which forms the shaped recess of the first wire end.

According to this embodiment, the wire is manufactured as a flexible tube, wherein an inside of the tube to the first wire end passes into the recess intended for connection to the first plug-in part. The tube may be cut or sliced at any desired point to form a resulting transverse end in which the corresponding plug-in portion can be attached. Therefore, the seton, in these embodiments, is easy to shorten when applied to the fistula channel, namely fistula tract, and forms a closed loop of the desired length.

The tube may be wholly or partially manufactured from the above-mentioned thermoplastic material. Fusion of the thermoplastic connection occurs when the heated portion of the thermoplastic tube is melted, so that the resulting smooth joint will be imparted with extra strength.

According to a further embodiment, the connecting means comprises a second recess provided on the second threaded end and provided with a second inner surface in the elongate longitudinal direction of the wire. The thermoplastic connecting body is provided with the first insertion part and a second insertion part with a second outside surface in the longitudinal direction of the wire which is at least partially conformed to the second recess.

The thermoplastic connecting body provides an intermediate pin structure, or plug structure, such that the first and second wire ends can connect to each other. In the example of the wire, manufactured as a flexible tube, the pin structure may be inserted through the inner diameter of the first and second end of the tube.

According to yet a further embodiment, the connecting body between the first insertion portion and the second insertion part has a cross-sectional thickening.

A "horizontal" nature of the thickening indicates a thickening in the plane perpendicular to the local longitudinal direction of the wire. This thickening is provided in a lateral clamping area with which the thermoplastic compound body simply could advance in a desired orientation within the receiving area of a melt clamp. In another aspect of the invention, by way of the connecting body being placed in the melt clamp in advance, it is not necessary to clamp the former during the placement of the seton when held by hand, and a resulting freedom of hand movement is beneficially exploited to slide the wire ends quickly and easily to the insertion portions of the connecting body in the melt clamp before it connects.

According to further embodiments, the thermoplastic connector body is optionally a different color in relation to that of the wire and the wire ends.

A visual contrast thereby achieved between the different color wire and wire ends on the one hand and the thermoplastic body on the other hand makes it possible to clamp the wire ends in place according to another aspect of the invention. According to another embodiment, the connecting means comprise a sleeve of thermoplastic material, wherein the wire ends can be placed in both outer sides so as to form a smooth connection.

In this embodiment, the smooth, closed loop is formed by the solid ends of the wire, namely without connecting means on the ends, being placed in a connection sleeve, and then by applying heat to the connection sleeve to melt it completely into the ends. The sleeve is optionally present in the clamp prior to the seton being closed, so that the positioning of the wire ends into the melt clamp is simplified.

According to one embodiment, the wire has a circular cross-section, with a wire diameter which is preferably in a range of 0.5 mm to 5 mm, and which is more optionally in a range of 1.5 mm to 2.5 mm, for example.

On account of the circular cross-section of the wire, a reduced, namely minimum, seton bending resistance will achieved in the direction of curvature for closing of the loop. In particular, a circular cross section results in an isotropic bending resistance without any preferential bending direction, and an independence of the local orientations of the tips on interconnection. An elliptical, for example an at least partially elliptical, or otherwise shaped cross-section for the wire is also possible pursuant to embodiments of the invention.

According to a second aspect, in accordance with the above effects and benefits, the invention provides a method of forming a closed loop from a seton suitable for treating a fistula, wherein the seton includes a wire having two wire ends, and wherein the method comprises:

forming a smooth connection by means of using connecting means for mutually connecting the ends in the longitudinal direction of the wire; and forming the seton to a smooth closed loop.

According to preferred embodiments, the method according to this aspect is used for non-therapeutic applications, in which the seton forms a smooth closed loop.

According to an embodiment of the method, the connecting means comprise a thermoplastic material, and the method also comprises:

providing a melt clamp provided with a receiving area for receiving the connecting means and the wire ends, and equipped with a melt source, for example a heat source, in the receiving area; and placing the connecting means and the wire ends into the receiving area in a cooperating manner, and then merging the connection means to form a smooth connection by way of applying the melt source, for example heat source.

By "melt source", it is meant a source which is operable to bring the thermoplastic material to the melting point in a controlled manner. Such melting can be induced by ways known to the skilled person, for example by supplying thermal energy from a heat source, by applying ultrasonic vibration from an ultrasonic, transducer, or by electromagnetic radiation.

According to further embodiments, the connecting means of the seton optionally comprise a separate thermoplastic connecting body, for example, a connector sleeve, or a connector or plug with a first and second plug-in part with any thickening in a middle portion thereof. A further embodiment includes a pre-placement of the thermoplastic connecting body in the receiving area of the melt clamp, and then placing recesses of the wire ends over and around the plug-in connection parts of the thermoplastic body. In this embodiment, the connecting body is not to be retained during deployment of the seton in a fistula channel, so that a user's hands installing the seton remain free for accurate positioning of the wire ends in the melt clamp.

According to a third aspect, the invention provides a clamp for melt-connecting the wire ends of the seton according to the first aspect, wherein the melting clamp comprises:

a pair of cooperating clamping members, provided with a receiving area for enclosing the connecting means in a closed condition of the clamping members; and a melt source in the receiving area, for supplying thermal energy to the connecting means, when present in the receiving area.

With such a clamp, it is possible to melt the thermoplastic connecting means in a very simple and controlled manner so as to form the seton with a smooth closed loop.

According to one embodiment, the melt clamp comprises a locking mechanism in closed position, when the connecting means is present in the receiving area, to clamp parts during supply of thermal energy thereto.

According to one embodiment, the melt clamp comprises a cooling element in the receiving area, for the extraction of thermal energy from the connecting means when in a connected state when present in the receiving area.

The use of the cooling element is to absorb the thermal energy associated with a previous step which is fed to the thermoplastic connecting means to melt it, after the formation of the wire connection. Thereby the thermoplastic material solidifies rapidly, so that the smooth connection can be realized very quickly.

According to a further embodiment, the melt comprises a clamp control unit for controlling at least one of the melt source, the cooling element, and the locking mechanism.

The control unit is capable of, for example, regulating the temperature in the receiving area and is optionally capable of informing the user of the terminal regarding the different stages of the melting process and the, for example expected, state of the wire ends and connecting means in the melt clamp.

According to one embodiment, the melting clamps are formed by a portable thermal wrench with arms equipped with clamping members and receiving area on the arm ends, wherein the arms are connected by way of hinges to the melting clamps which are manually adjusted into a closed state.

BRIEF DESCRIPTION OF THE FIGURES

Next, exemplary embodiments of the invention, only in way of example, will be described with reference to the accompanying diagrammatic drawings, in which corresponding parts designated by corresponding reference symbols are shown; in respect of the accompanying diagrammatic drawings.

The drawings are only intended for illustrative purposes, and should not limit the scope of protection which is defined by the claims.

DESCRIPTION OF EMBODIMENTS

Figure 1:
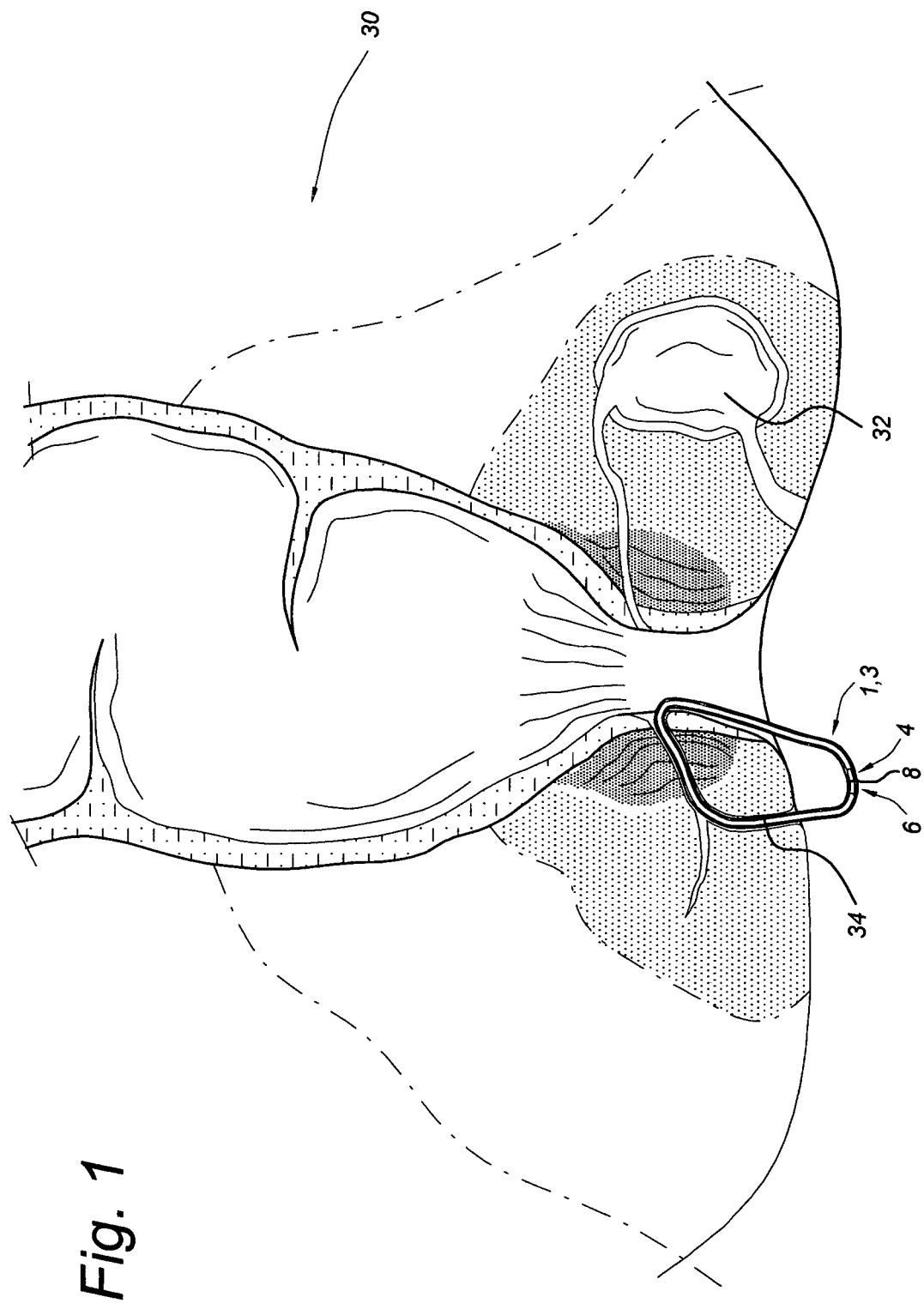
FIG. 1 is an illustration of an embodiment of a seton formed into a smooth closed loop according to the first aspect of the invention.

Referring to FIG. 1, there is shown an embodiment of a seton 1 for treating a fistula 32 according to a first aspect of the invention. The seton 1 is disposed in a fistula channel 34 of a patient 30 and comprises a wire having a first wire end 4 and a threaded second end 6 which are formed together to provide a smooth connection 8, so that the seton 1, when applied, forms a smooth closed loop 3. The smooth connection 8, and the smooth closed loop 3 are provided by embodiments of the seton 1 which can be realized, of which some will be further explained below.

Figure 2A:
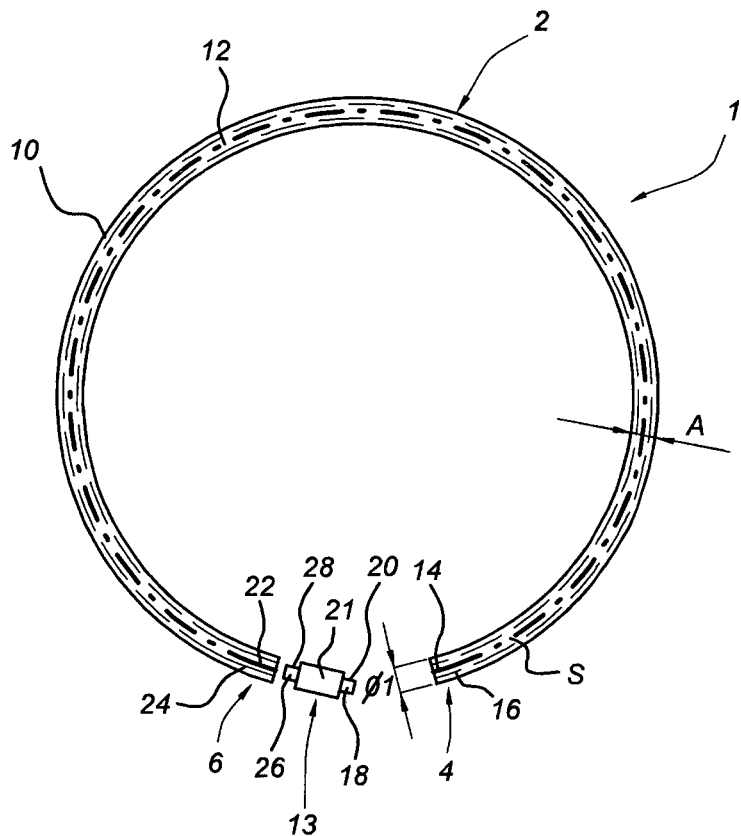
FIG. 2a, FIG. 2b and FIG. 2c are illustrations of an embodiment of a seton in an open state.

In FIG. 2a, there is shown an illustration of an embodiment of a seton 1 in a non-closed state. The seton 1 comprises a seton wire 2 which is manufactured from a flexible tube 10 with an inner surface 12 to a first wire end 4 which merges into a first recess 14 with a first inner surface 16 in the local longitudinal direction S of the wire 2. At a second wire end 6, the inner surface 12 merges into a second recess 22, with a second inner surface 24 in the local longitudinal direction S of the wire 2. The illustrated tubular wire 2 has a circular cross-section A, with an outer diameter Ø1 for example, which has a value of about 1.67 mm, namely substantially "5 french". The tube 10 is optionally easily shortened to a desired length before the wire ends 4, 6 are mutually connected. A connecting arrangement, namely connecting means, of the seton 1 is partially formed by the first and second recesses 14, 22, and partly by a thermoplastic connection body 13 in the form of a plug connection having a transverse thickening 21. This connection plug 13 is optionally implemented by inserting a first insertion portion 18 and a second insertion portion 26 into the first recess 14, and into the second recess 22 respectively. Outer surfaces 20, 28 of such engaging pieces 18, 26 are shaped in a complementary manner to the first and second recesses 14, 22, so that these can be inserted tightly into each other. The thermoplastic material of the connection plug 13 is, for example, made from a thermoplastic material, such as polyurethane or polycarbonate. The tube 10 is also manufactured here from such a thermoplastic material. The thermoplastic connection plug 13 can be in a different color relative to that of the tube 10, and also to that of the wire ends 4, 6. By supplying thermal energy to the plug 13, which is inserted into the recesses 14, 22, the wire ends 4, 6 of the seton 1 and the plug 13 form a ridged connection 8 which is melted together, namely thermally fused.

Figure 2B:
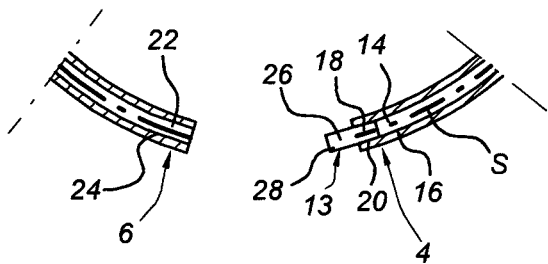

In FIG. 2b, there is shown another embodiment of the seton 1, which is substantially identical to the embodiment shown in FIG. 2a, but in which the connecting body 13 is formed differently. The connecting body 13 is formed here as a connecting pin 13 manufactured from a thermoplastic material, for example as elucidated in the foregoing. The connecting pin 13 has a first insertion portion 18 and a second insertion portion 26 with first and second outer surfaces 20, 28 that overlap, without an intermediate transverse thickening 21. The wire ends 4, 6 may therefore be in direct contact during mutual connection by means of the connecting pin 13.

Figure 2C:
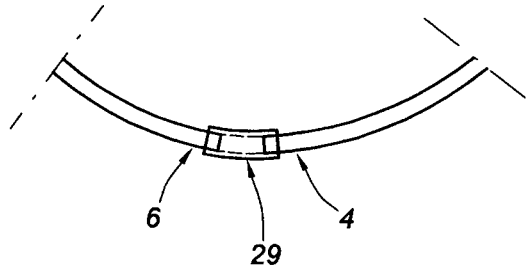

According to another embodiment shown in FIG. 2c, the wire 2 and the wire ends 4, 6, are solid and cylindrical, and the connecting means comprise a sleeve 29 of thermoplastic material. The sleeve 29 is provided with a sleeve inside that closes outside edges of both wire ends 4, 6 when placed in position. As a result, the sleeve 29, through supplying thermal energy, can be plastically deformed together with the wire ends 4, 6 to form the smooth connection 8.

In a further embodiment (not shown), the wire 2 is formed as a solid cylindrical structure with a cylindrical second wire end that forms the first plug-in part, and with the first wire end having a thickened thermoplastic compound structure that contains a cylindrically shaped first recess along the longitudinal direction of the wire, wherein the cylinder-shaped first insertion part can be received. By melting the thickened connection structure around the second wire end, the smooth connection is thereby formed. The length of the cylindrical wire that is desired to be advanced to the second wire end can be shortened, for example by a cutting operation.

The seton 1 described in the foregoing, together with alternative embodiments of the seton 1 according to the first aspect, can be manufactured into a smooth, closed loop 3 in the longitudinal direction S of the wire 2, by forming of the wire ends 4, 6 and connecting means 13-28 to form a smooth connection 8. Such a seton 1 with the smooth connection 8 can be, for example, achieved by means of a melt clamp 40 according to a third aspect, one of which embodiment is described below in detail.

Figure 3:
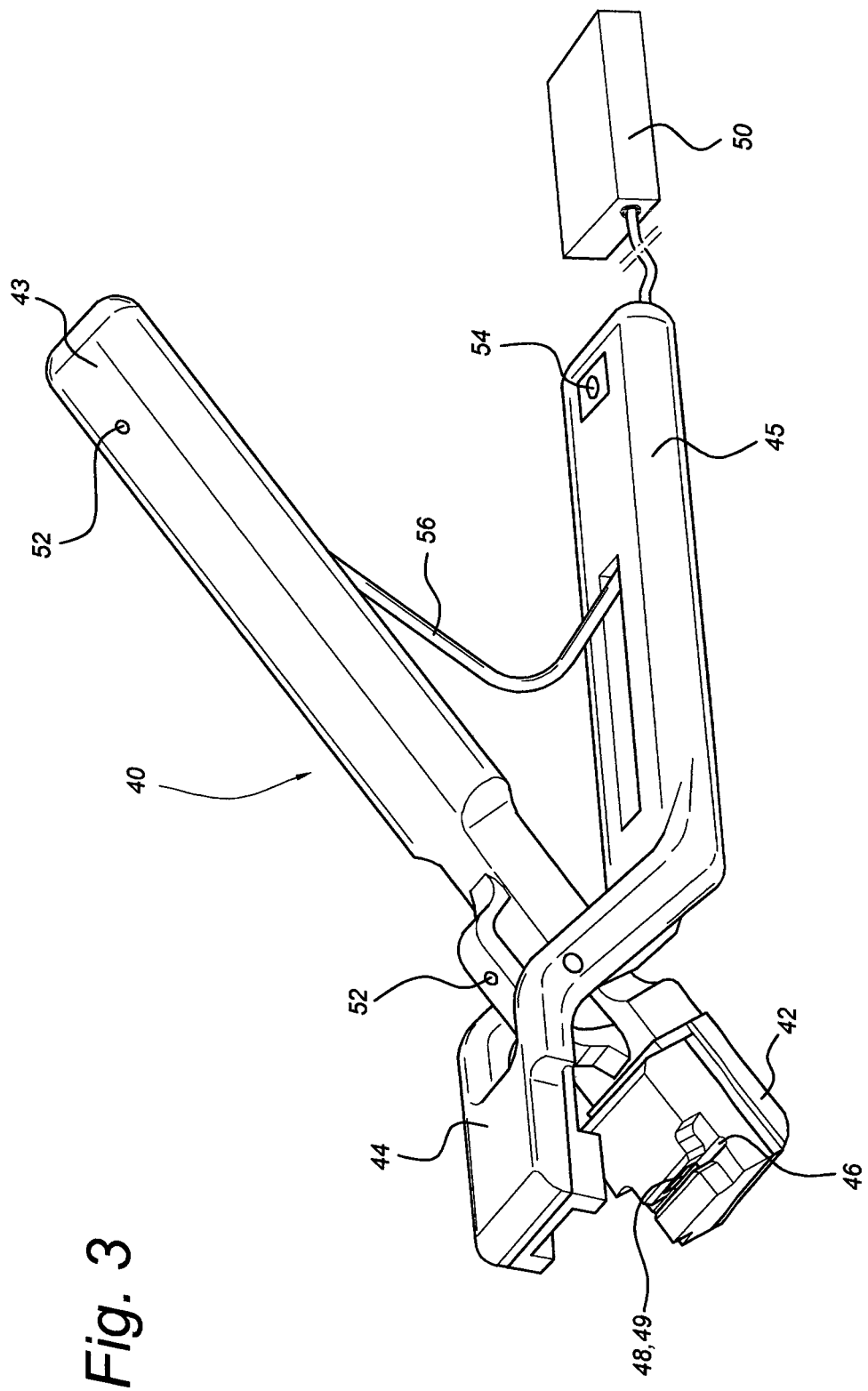
FIG. 3 is an illustration of an embodiment of a melt clamp according to the third aspect of the invention.
Figure 3A:
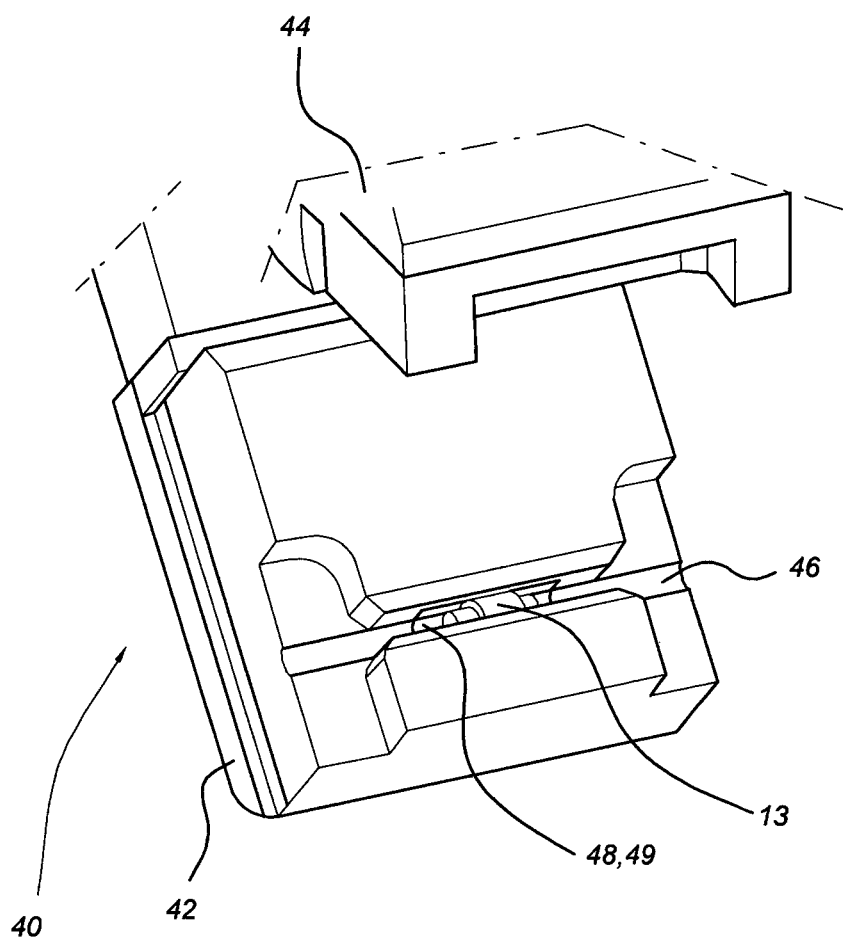
FIG. 3a is an illustration of a part of the embodiment of a fuse terminal from FIG. 3.

In FIG. 3 and FIG. 3A, there are shown illustrations of an embodiment of a melt clamp 40. According to this third aspect of the invention, a portable melt clamp 40 is provided with arms 43, 45 which are pivotally connected to form a clip, so that the melt clamp can be manually brought to a closed state. The arms 43, 45 of the portable melt clamp 40 provide a pair of compressible ends, namely clamping parts 42, 44, which are provided with a receiving region 46 for enclosing the seton connecting means when the clamp parts 42, 44 are in a closed condition. According to a corresponding method, the method includes placing the wire ends 4, 6 of the seton 1 into the first receiving region 46.

The portable melt clamp 40 comprises a melt source 48 in the receiving area 46, adapted for applying thermal energy to the connecting means. By employing such a fusing terminal provided by way of the portable melt clamp 40, it is possible, in a very simple manner, to form the thermoplastic material in the connecting means of the seton 1 to provide a smooth joint 8 in a controlled manner.

The portable melt clamp 40 has a locking mechanism 54 for holding the clamping members 42, 44 in a closed state when supplying thermal energy to the connecting means, when present in the receiving area 46. The portable melt clamp 40 is optionally provided with a spring element 56 to force the arms 43, 45 mutually away from each other, thereby causing the clamping parts 42, 44 to open, for example, when the locking mechanism 54 is turned off. Moreover, the portable melt clamp 40 optionally comprises a cooling element 49 in the receiving area 46, for extracting thermal energy from the connecting parts when in a smooth mutually connected state.

The portable melt clamp 40 has a control unit 50 for controlling the melt source 48, the cooling element 49, and the locking mechanism 54. By using the cooling element 49, the thermal energy associated with a previous step fed to the thermoplastic connecting means can be removed, after formation of the smooth wire connection. Such an approach enables the thermoplastic material to solidify faster, so that the smooth connection can be achieved very quickly.

In FIG. 3a, there is shown the first and second clamping members 42, 44 of the melt clamp 40. As shown, a separate thermoplastic connection body 13, here a connect plug with transverse thickening as in FIG. 2a, may be placed in the receiving area 46. According to an embodiment of the method, the method includes placing the thermoplastic connection body 13 in advance in the receiving area 46 of the portable melt clamp 40. The method further includes then passing the wire 2 of the seton 1 through a desired channel, for example by pulling through the fistula channel 34, and eventually shortening the wire 2 to a desired length. Thereafter, the method includes placing the wire ends 4, 6 with the recesses 14, 22 into the melt clamp 40 over and around the insertion portions 18, 26 of the thermoplastic connection body 13. In this embodiment, the connection body 13 does not need to be held during positioning of the seton 1 in a fistula tract 34, so that the hands of a person applying the seton 1 remain free for accurate positioning of the wire ends 4, 6 in the melt clamp 40. Subsequently, the method includes closing the melt clamp 40, and thereafter activating the melt source 48. After the wire ends 4, 6 and connecting body 13 are connected with each other in a smooth connection 8, the method includes cooling the whole setup by means of the cooling element 49. During the whole process, the locking mechanism 54 keeps the clamping members 42, 44 closed. The optical indicator 52 may be functionally lit with multiple colored LEDs to indicate various stages of the operation of the melt clamp. Audible sounds may also be used as indicators.

It will be appreciated that the above described embodiments, are described only by way of example and not limiting in any sense, and that various changes and modifications are possible without departing from the scope of the invention and that the scope is determined only by the appended claims.

LIST OF REFERENCE SIGNS

| | | |
|---|---|---|
| 1: seton | 20: first outer surface | 43: first arm |
| 2: wire | 21: transverse thickening | 44: the second clamping part |
| 3: smooth closed loop | 22: the second recess | 45: second arm |
| 4: first wire end | 24: the second inner surface | 46: receiving area |
| 6: second wire end | 26: the second insertion portion | 48: melt source |
| 8: smooth connection | 28: second outer surface | 49: cooling element |
| 10: tube | 29: sleeve | 50: control unit |
| 12: inner surface | 30: patient | 52: optical indicator |
| 13: thermo-plastic connection body | 32: fistula | 54: locking mechanism |
| 14: the first recess | 34: fistula tract | 56: spring |
| 16: first inner surface | 40: melt clamp | |
| 18: first insertion portion | 42: first clamping means | |
| A: cross section | S: longitudinally | Ø1: first diameter |

REFERENCES

[1] DROP, J G. '*Integrated Circuit Personalization at the Module Level*', IBM tech. dis. bull. October 1974, Vol. 17, No. 5, p. 1344-1345, ISSN 2345-6789.

The invention claimed is:

1. A seton for treating a fistula, comprising:
a wire having an elongate and flexible tubular structure on the order of ten times longer than it is wide, a first wire end, a second wire end and an inner surface extending in a longitudinal direction from a first wire end inner surface to a second wire end inner surface; and
a connection body including a first insertion portion having a first outer surface in the longitudinal direction of the wire at least partially conformed to the first wire end inner surface enabling a smooth connection in the longitudinal direction of the wire such that the seton becomes a smooth, closed loop.

2. The seton as set forth in claim 1, wherein the connection body, the wire or both include a thermoplastic material for providing the smooth connection.

3. The seton as set forth in claim 1, wherein the connection body, the wire or both include a light-curable material for providing the smooth connection.

4. The seton as set forth in claim 1, wherein the connection body, the wire or both include a chemically-curable material for providing the smooth connection.

5. The seton as set forth in claim 1, wherein the wire is formable in shape.

6. The seton as set forth in claim 1, wherein the wire has a circular cross-section, with a wire diameter optionally in a range of 0.5 mm to 5 mm, and more optionally in a range of 1.5 mm to 2.5 mm.

7. The seton as set forth in claim 1, wherein cutting of the wire to adjust wire length does not affect the smooth connection or the seton becoming the smooth, closed loop.

8. The seton as set forth in claim 1, wherein the connection body is further provided with a second insertion part having a second outer surface in the longitudinal direction of the wire which is at least partially conformed to the second wire end inner surface recess to support the smooth connection in the longitudinal direction of the wire.

9. The seton as set forth in claim 8, wherein the connection body between the first insertion part and the second insertion part comprises a transverse thickening.

10. The seton as set forth in claim 8, wherein the connection body has a different color relative to one or more colors of the wire and the wire ends.

11. The seton as set forth in claim 1, wherein the connection body provides an intermediate pin structure or plug structure, such that the first and second wire ends can connect with each other.

12. The seton as set forth in claim 1, wherein the connection body is substantially shorter than the wire.

13. The seton as set forth in claim 12, wherein the connection body has a length no more than half that of the wire.

14. The seton as set forth in claim 1, wherein the wire and the connection portion provide a smooth connection in the longitudinal direction of the wire such that the seton becomes the smooth, closed loop with a substantially constant cross-section at the connection.

* * * * *